United States Patent [19]

Balint, Jr. et al.

[11] Patent Number: 4,801,449
[45] Date of Patent: Jan. 31, 1989

[54] METHOD FOR TREATMENT OF KAPOSI'S SARCOMA

[75] Inventors: Joseph P. Balint, Jr., Seattle; Frank R. Jones, Edmonds, both of Wash.

[73] Assignee: IMRE Corporation, Seattle, Wash.

[21] Appl. No.: 948,268

[22] Filed: Dec. 31, 1986

Related U.S. Application Data

[63] Continuation-in-part of Ser. No. 690,781, Jan. 11, 1985, Pat. No. 4,681,870.

[51] Int. Cl.⁴ .................. G01N 33/552; G01N 33/543; B01D 15/08
[52] U.S. Cl. ..................................... 424/85.8; 424/88; 436/518; 436/523; 436/527; 210/656; 210/927; 530/413
[58] Field of Search ................ 424/85, 88; 210/691, 210/927, 905, 656; 514/8, 21; 530/825, 350, 388, 371, 810; 436/518, 523, 527

[56] References Cited

PUBLICATIONS

Terman et al., "Preliminary Observations of the Effects on Breast Adenocarcinoma of Plasma Perfused Over Immobilized Protein A," *New Eng. Journ of Med*, 305:1195–1200, Nov/1981.

Holohan et al., "Regression of Canine Mammary Carcinoma After Immunoadsorption Therapy" *Cancer Research* 42:3663–3668, Sep./1982.

Kiprov et al., "Extracorporeal Perfusion of Plasma over Immobilized Protein A in a Patient with Kaposi's Sarcoma and Acquired Immunodeficiency", *Journ. of Biol. Res, Mod.*, 3:341–346, 1984.

Bansal et al., "Ex Vivo Removal of Serum IgG in a Patient with Colon Carcinoma", *Cancer*, vol. 42, pp. 1–18, Jul./1978.

Messerschmidt et al., "Phase I Trial of *Staphylococcus Aureus* Cowan I Immunoperfusion" *Cancer Treatment Reports*, vol. 66, No. 12, pp. 2027–2031, Dec./1982.

Besa et al., "Specific Immunoadsorption of IgG Antibody in a Patient with Chronic Lymphocytic Leukemia and Autoimmune Hemolytiz Anemia" *Am. Journ. of Med*, vol. 71, pp. 1035–1040, Dec./1981.

*Primary Examiner*—John Kight
*Assistant Examiner*—Nathan M. Nutter
*Attorney, Agent, or Firm*—Townsend & Townsend

[57] ABSTRACT

An immunoadsorbent material for removing IgG and IgG-complexes from biological fluids is prepared by covalently binding protein A to a solid-phase silica matrix. It has been found that particularly stable, high-capacity immunoadsorbents are obtained by derivatizing the silica with amino and/or carboxyl groups, and reacting the protein A with a carbodiimide at a pH in the range from 3.5 to 4.5. Binding through free hydroxyl groups may be achieved with cyanogen halides at a pH in the range from 11.0 to 11.5. After acid washing (pH 2.0–2.5) to remove non-covalently bound protein A, the immunoadsorbent may be employed in a column for therapeutic treatment of various cancers and autoimmune disorders where IgG-complexes are implicated as suppressing factors in inhibiting a normal immune response. The column has been successfully employed in treating patients suffering from Kaposi's sarcoma.

10 Claims, 2 Drawing Sheets

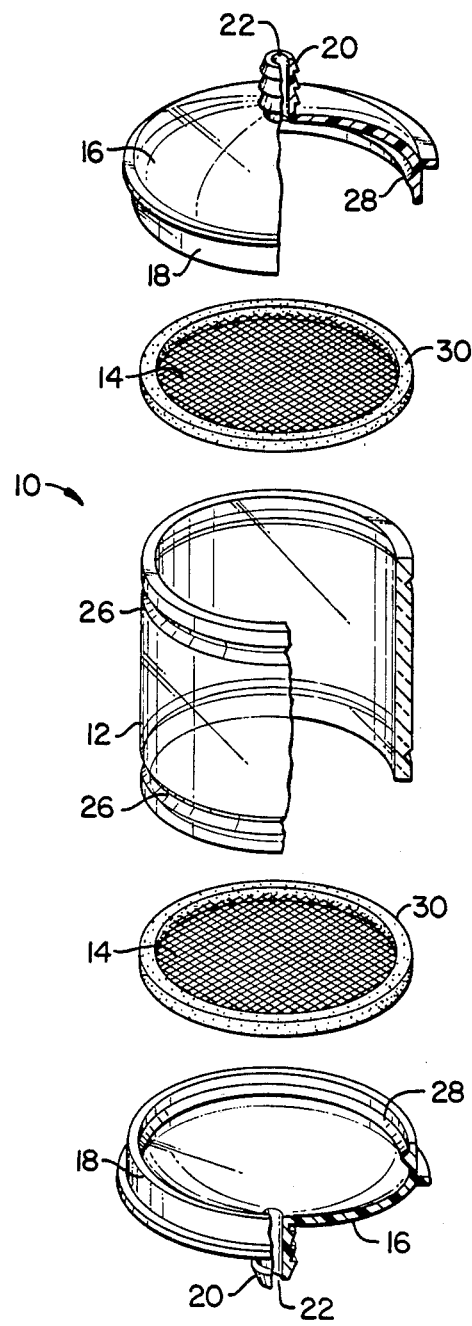
FIG._1.

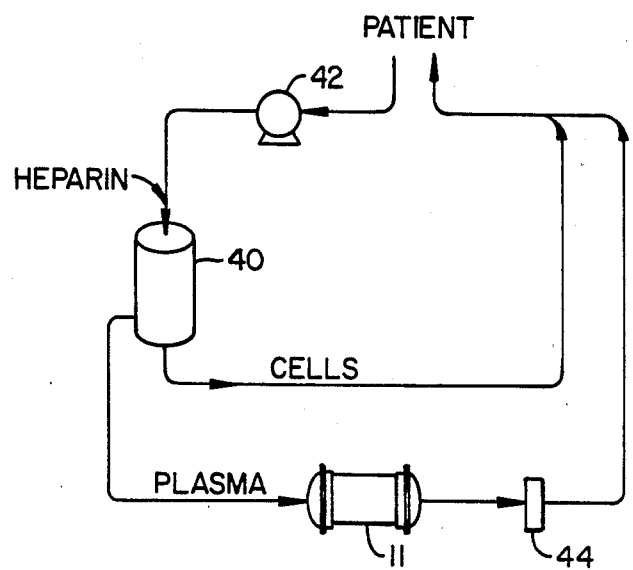
FIG._2.

METHOD FOR TREATMENT OF KAPOSI'S SARCOMA

BACKGROUND OF THE INVENTION

This application is a continuation-in-part of application Ser. No. 690,781, filed on Jan. 11, 1985 and now U.S. Pat. No. 4,681,870.

1. Field of the Invention

The extracorporeal treatment of blood to remove immunoglobulins and circulating immune complexes may be useful in a variety of circumstances. For example, it is suspected that some cancer patients develop a particular immune complex consisting of the patient's own IgG and an antigen associated with the cancer. It is thought that such complexes can interfere with the functioning of the patient's immune system and prevent the immune system from responding to the cancer. Treatment of various cancers, including carcinomas and sarcomas, using extracorporeal plasma perfusion to remove immune complexes has yielded varying levels of success.

Kaposi's sarcoma is a highly malignant cancer of the connective tissue occurring usually in the skin and sometimes in the lymph nodes or viscera. The disease is uncommon in healthy individuals, but occurs frequent in immunocompromised individuals, particularly those suffering from acquired immunodeficiency syndrome. No satisfactory treatment for Kaposi's sarcoma presently exists.

It would thus be desirable to provide a treatment for Kaposi's sarcoma which would result in stabilization remission or cure of the disease.

2. Description of the Relevant Art

Heat and formalin-treated *Staphylococcus aureus* Cowan I packed in the column has been employed as a therapy for neoplastic disease based on the removal of immune complexes from blood. See, e.g., Bansal et al. (1978) Cancer 42: 1–18; Terman et al. (1981) N. Engl. J. Med 305: 1195–1200; Jones et al. (1980) Cancer 46: 675–684; Ray et al. (1980) Cancer 45: 2633–2638; Besa et al. (1981) Am. J. Med. 71: 1035–1040; Holohan et al. (1982) Cancer Res. 42: 3663–3668; Messerschmidt et al. (1982) Cancer Treat. Rep. 66: 2027–2031; MacKintosh et al. (1983) West. J. Med. 139: 36–40; Snyder et al. (1982) J. Immunol. 128: 2726–2730; and Jones et al. (1984) J. Biol. Resp. Mod. 3: 286–292. Terman et al. (1981) N. Engl. J. Med. 305: 1195–1200 describes use of an immunoadsorbent consisting of protein A entrapped within a charcoal matrix for treatment of cancer patients. The experimental work reported in the present application was published in Kiprov et al. (1984) J. Biol. Resp. Mod. 3: 341–346.

SUMMARY OF THE INVENTION

The present invention provides a method for the treatment of patients suffering from Kaposi's sarcoma. It has been found that the extracorporeal removal of immune complexes and immunoglobulin from the blood of a Kaposi's sarcoma patient can bring about substantial remission of the disease, including reduction in the size of skin lesions and healing of ulcerated skin lesions. Extracorporeal removal of immune complexes and immunoglobulin may be achieved by withdrawing blood from the patient, separating the blood into its plasma and serum components, contacting the plasma with an immunoadsorbent specific for the immune complexes and immunoglobulin, and reinfusing the treated plasma and cellular blood components to the patient. The immunoadsorbent is preferably protein A covalently bound to an inert matrix, usually silica. The treatments are usually repeated periodically until a desired response has been achieved.

BRIEF DESCRIPTION OF THE DRAWINGS

FIG. 1 is an exploded view of the immunoadsorbent column of the present invention.

FIG. 2 is a diagrammatica representation of a system for the extracorporeal treatment of blood constructed according to the present invention.

DESCRIPTION OF THE SPECIFIC EMBODIMENTS

An immunoadsorbent column having a novel immunoadsorbent material therein is provided for the extracorporeal treatment of a biological fluid, such as plasma, to remove IgG and IgG-complexes therefrom. The treatment may be provided by continuously removing a patient's blood, separating the blood cells therefrom, treating the separated plasma in the immunoadsorbent column to remove the IgG and IgG-complexes, and mixing and returning the treated plasma and blood cells directly to the patient. Alternatively, after the blood has been removed and the blood cells separated, the blood cells may be directly reinfused into the patient. The separated plasma may be collected, treated in the immunoadsorbent column of the present invention, again collected and then returned to the patient as early as possible.

The novel immunoadsorbent material of the present invention comprises protein A covalently coupled to a solid-phase silica matrix under particular conditions which have been found to maximize activity of the protein A and binding capacity of the column while minimizing leakage of the protein A and other substances from the column during use.

Protein A is cell surface protein which is isolated from paticular strains of *Staphylococcus aureaus* and able to bind free IgG and IgG-complexes. IgG-complexes are antigen-IgG complexes which circulate in patient serum and are not removed by the normal phagocytic mechanisms of the immune system. As stated above, removal of such circulating IgG-complexes is useful in the treatment of a variety of disorders, including autoimmune disorders and cancer. The immunoadsorbent material of the present invention will have a binding capacity of at least 5 mg IgG/gm adsorbent, usually 7 mg/gm or greater. The immunoadsorbent system of the present invention allows removal of up to about 750 to 1500 mg of the circulating IgG-complexes, usually about 1000 mg by treatment of the plasma.

Protein A may be obtained from cultures of *Staphylococcus aureus*, for example *S. aureus* Cowan I, by harvesting the cells and lysing with a suitable lytic agent, such as lysostaphin. The protein A may then be purified by any suitable technique, such as ion exchange combined with molecular sieve chromatography, to a final purity of 90–99%, usually about 95%. Alternatively, suitably purified protein A may be obtained from a number of commercial suppliers, such as IMRE Corporation, Seattle, Wash.

The solid-phase silica matrix may comprise virtually any form of particulate silica including amorphous silicas, such as colloidal silica, silica gels, precipitated silicas, and fumed or pyrogenic silicas; microcrystalline silicas such as diatomites; and crystalline silicas such as quartz. The silica should have a particle size in the range from about 45 to 120 mesh, usually in the range from 45 to 60 mesh.

In the preferred embodiment, the solid-phase matrix of the immunoadsorbent material will be formed from diatomite aggregates. Usually, the diatomite material will be calcined to remove any remaining organic material and to harden the surface of the aggregates in order to lessen breakage and degradation of the immunoadsorbent during use. The diatomite material will consist primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other mineral. Other impurities may be present in the diatomite, but care should be taken that such impurities are non-toxic and non-degradative to the biological fluid being treated. A particularly suitable solid-phase silica (diatomite) matrix may be obtained from Johns-Manville Corporation under the tradename Chromosorb ®.

The protein A is covalently coupled to the solid-phase silica matrix by derivatizing the matrix to introduce active reactive functional groups, and reacting the derivatized matrix with a coupling agent or under chemical conditions which binds the protein A to the matrix. Exemplary protocols for such binding are as follows.

Amino groups may be introduced to the silica matrix as the reactive functional group by any suitable method. For example, the silica matrix is first acid washed, followed by extensive rinsing with water and drying. The acid washed silica is then reacted in a 5% to 10% solution of an aminosilane, such as γ-aminopropyltriethoxysilane, with the pH adjusted to about 3.0. After 2 hours at about 75° C., the silica matrix is again washed extensively with water and dried overnight at 100° C.

Carboxyl groups may be introduced to the silica matrix as the reactive functional group by further reacting the amino-derivatized material, as just described, with succinic anhydride as follows. The silica matrix is mixed with succinic anhydride in a suitable buffer, such as 0.5M phosphate buffer, and the pH adjusted to about 6.0. After 12 to 16 hours at room temperature, the silica matrix is extensively washed, and dried.

Hydroxyl group (in addition to those hydroxyl groups occurring in the native structure of the matrix) may be introduced to the silica matrix by any suitable method. For example, the silica matrix is first acid washed, rinsed extensively with water, and dried. The acid washed silica is then reacted in a 5–10% solution of a silane such as γ-glycidoxypropyltrimethoxysilane. After a 2 hour incubation at 75° C., the silica matrix is again washed extensively with water and dried at 100° C.

Once the silica matrix has been derivatized with either amino and/or carboxyl groups, the protein A is introduced by reaction with a carbodiimide which forms a covalent link between the matrix and the protein A. The carbodiimide will have the formula:

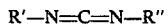

where R' and R" may be the same or different, being either alkyl, substituted-alkyl, benzyl, substituted-benzyl, or hydrogen. Alkyl or substituted-alkyl may be straight, branched or cyclic, and R will usually have fewer than 16 atoms other than hydrogen, more usually fewer than 12 atoms, and six or fewer heteroatoms (i.e., other than carbon and hydrogen). If substituted-benzyl, R will usually have three or fewer substitutions which will typically be halogen atoms. Suitable carbodiimides are well known in the art. The preferred carbodiimide is 1-cyclohexyl-3-(2-morpholinoethyl)carbodiimide metho-p-toluenesulfonate.

The binding reaction for the amino-derivatized matrix is carried out under the following conditions. The protein A is mixed in water in the presence of thwe carbodiimide. The pH of the solution is adjusted to the range from 3.5 to 4.5, usually about 3.5, and the silica matrix is introduced and gently mixed for an extended period, usually about 15 to 30 hours, more usually about 20 to 25 hours at room temperature. The matrix is then extensively washed with water, dried, and acid washed at a pH from about 2.0 to 2.5, usually about 2.25, to remove labile protein and other substances which are non-covalently bound to the silica matrix. The material is then finally washed, dried and checked for the presence of pyrogens. A suitable test for the presence of pyrogens is the limulus ambeocyte lystate (LAL) test, commercially available as a kit from Marine Biologicals, Inc., P.O. Box 546, Marmora, N.J. 08222.

The binding process for the carboxyl-derivatized silica matrix is as follows. A carbodiimide (as above) is dissolved in water, and the solution is adjusted to a pH in the range from 3.5 to 4.5, usually about 3.5 pH. After introducing the silica matrix, the solution is gently mixed for an extended period, usually about 10 to 25 hours, more usually about 12 to 20 hours, at room temperature. The silica matrix is then removed and extensively washed with water. The protein A is then dissolved in water, the pH adjusted to the range from 3.5 to 4.5, usually about 3.5, and the silica matrix added and mixed for about 15 to 30 hours, usually about 20 to 25 hours at room temperature. The silica matrix is then extensively washed with water, dried, and washed one time in an acid wash (pH 2.0 to 2.5, usually about 2.25) to remove non-convalently bound protein A and other substances. The silica matrix is then washed a final time, and checked for pyrogens.

The binding process for the hydroxyl derivatized silica matrix is as follows. Cyanogen bromide is dissolved in water. The silica matrix is added to water and the pH is adjusted to 11.0. The cyanogen bromide solution is added to the silica matrix, the mixture is constantly stirred keeping the silica particles is suspension, and the pH is maintained between 11.0 and 11.5 by addition of NaOH until pH stabilization occurs. The activated silica matrix is extensively washed with water, mixed with a solution of protein A with the pH adjusted to 8.5–9.0, and mixed overnight at 25° C. After coupling, the matrix is washed extensively with water, dried, and washed one time in an acid wash, pH 2.5, to remove non-covalently bound and acid labile protein A linkages. The silica matrix is washed a final time and checked for pyrogens.

As demonstrated in the Experimental section hereinafter, the pH range of from 3.5 to 4.5 for binding of the protein A to the amino and/or carboxyl functionalities on the silica matrix is critical. Similarly, the binding of the protein A to the hydroxyl functionalities at a pH in the range from 8.5 to 9.0 is also critical. The efficiency of binding and the retained activity of the protein A both diminish as the pH deviates outside of these narrow ranges. Moreover, it has been found that a mild acid wash with a pH in the range from about 2.0 to 2.5 successfully removes non-covalently bound substances from the silica matrix, particularly cleaving labile protein A linkages. The acid treatment is thus important in achieving a stable immunoadsorbent material which is able to retain the IgG and IgG-complexes bound within the column and avoid loss of protein A into the serum being treated.

Referring now to FIG. 1, the construction of a suitable cartridge 10 for containing the immunoadsorbent material as just described is illustrated. The cartridge comprises a cylinder 12, a pair of retaining screens 14, and a pair of end caps 16. The end caps 16 each include a flange element 18 projecting from one surface thereof and a connector nipple 20 projecting from the other surface thereof. The connector nipple includes an axial passage 22 therethrough to define inlet/outlet ports through the end caps 16.

The cylinder 12 includes an annular groove 26 at each end thereof. The flange element 18 on each end cap includes a mating ring 28 on the inner cylindrical surface thereof, which mating ring engages the annular groove 26 when the caps are placed over the end of the cylinder 12. Each screen 14 includes a gasket 30 around its circumference, which gasket serves as a sealing member between the end cap 16 and the cylinder 12 when the cartridge 10 is assembled. To assemble the cartridge 10, a first screen 14 is placed over one end of the cylinder 12, and an end cap 16 is fitted over the screen 14. The cylinder 12 is then filled with the immunoadsorbent material as described above, and assembly of the cartridge completed by placing the remaining screen 14 and end cap 16 in place.

The dimensions of the cartridge 10 are not critical, and will depend on the desired volume of immunoadsorbent material. The volume of the cylinder 12 will typically range from about 50 to 500 cc, having a diameter in the range from about 4 to 8 cm and a length in the range from about 5 to 10 cm.

A column 11 (FIG. 2) which comprises a cartridge 10 containing a suitable amount of the immunoadsorbent material prepared as described above, may be sterilized, typically with a gas sterilant such as ethylene oxide, and either used immediately or sealed and stored for later use.

Prior to use, the column 11 will be washed with normal saline followed by a wash with normal saline containing heparin or other suitable anti-coagulant such as anti-coagulant citrate dextrose (ACD). The column 11 may then be connected to a cell separator 40 (FIG. 2) to receive separated plasma therefrom. The cell separator 40 may be a continuous flow cell separator, such as an IBM Model 2997, available from IBM, Armonk, N.Y., or may comprise a semi-permeable membrane which allows passage of the plasma and blood proteins, but prevents passage of the cellular elements of the blood. In the case of a semi-permeable membrane, a blood pump 42 will be required to pass the blood through the membrane. Suitable blood pumps include a tube and peristaltic pumps where the blood is isolated from the pumping machinery to prevent contamination. The blood will pass through the cell separator 40 at a rate in the range from about 10 to 20 ml/min typically until a total volume of about 2 liters of blood have been passed. The blood cells are mixed with the plasma passing from the treatment column 11, and the recombined blood returned to the patient. Typically, a microfilter 44 is provided at the outlet of the treatment column 11 to prevent passage of macroscopic particles which might be lost from the column 11.

The following examples are offered by way of illustration and not by way of limitation.

EXPERIMENTAL

1. Prearation of Immunoadsorbent Material

Acid washed silica matrix (Chromosorb ® P, No. C5889, Johns-Manville, 1.25 kilograms) was weighed out, divided into 4 parts, and added to four Fernback type flasks. The matrix was re-hydrated with water and vigorously shaken overnight in a gyrotary shaker at approximately 150 rpm. After this procedure, the silica matrix was extensively washed with water to remove generated fine particles. This procedure appeared to make the shape of the silica matrix particles more uniform resulting in matrix particles which generate few fines in later handling procedures. After washing, the silica matrix was added to an approximately 5–10% solution of appropriate silane, incubated for 2 hours at 75° C., extensively washed with water, and baked dry at 115° C.

The dried silanized silica matrix (1 kilogram) was re-hydrated and extensively washed with water to remove generated fines. The silica matrix was then mixed with 2 grams of protein A and 50 grams of carbodiimide (1-cyclohexyl-3-(2-morpholinoethyl)carbodiimide metho-p-toluenesulfonate) and the pH of the mixture adjusted to 3.5. Our studies indicated that a pH range of 3.5–4.5 yields a higher percentage uptake of protein A versus a higher pH range (4.5–5.0) (77.42% uptake versus 67.49%). A lower pH range, below 3.5 was avoided because of possible acid hydrolysis of protein A during the prolonged binding incubation.

The mixture was gently rotated on a roller apparatus for 22 hours at 25° C. The silica matrix was then extensively washed with water, dried at 37° C., and the uptake of protein A was determined. After drying, 3 liters of acid water, pH 2.5, was added to the silica matrix, incubated for 5 minutes at 25° C., and the amount of protein A released from the matrix was determined. The matrix was extensively washed with water, dried, and the amount of protein A per gram of silica was determined. The results were as follows:

| Bound Protein A | 1966 mg |
| Protein A released | 440 mg |
| Protein A/gm adsorbent | 1.5 mg |

2. Use of Immunoadsorbent to Separate IgG and IgG Complexes from Normal Human Serum Immunoadsorbent prepared as described above was incubated with 2 ml of normal human serum for 5 minutes at 25° C. After incubation, the silica matrix was washed with 100 ml of phosphate buffered saline (PBS), pH 7.5. Bound proteins were eluted with 12.5 ml of PBS, pH 2.5, and neutralized to pH 7.5. The total protein eluted was determined to be approximately 10 mg, as described by Lowry et al. (1951) J. Biol. Chem. 193: 265–272. The eluted protein was subjected to polyacrylamide gel electrophoresis, and prominent bands were detected a 50 kD and 25 kD, corresponding to the heavy and light chains of IgG, respectively. The presence of IgG was confirmed by double immunodiffusion analysis employing γ-chain specific anti-human IgG.

To determine removal of IgG complexes by the immunoadsorbent, 2.5 ml of normal human serum was incubated with heat-aggregated human IgG to fix complement to the aggregates. This combination behaves as immune complexed IgG. Immunodsorbent prepared as described above was incubated with 0.8 ml of the heat-aggregated serum for 5 minutes at 25° C. This was repeated 3 times until a total volume of 2.4 ml was passed through the immunoadsorbent, and fractions were collected until all the serum was passed through the immunoadsorbent. IgG immune complexes in pre- and post-perfusion serum fractions were measured employing the Raji cell binding IgG immune complex assay as described by Theofilopoulos et al. (1974) J. Exp. Med. 140: 1230-1244. The results are presented in Table 1.

TABLE 1

| Sample* | Immune Complex (μg/ml) | % Reduction |
|---|---|---|
| Pre-perfusion | 160 | — |
| Post-perfusion- | | |
| Fraction 1 | 120 | 25 |
| Fraction 2 | 125 | 22 |
| Fraction 3 | 105 | 34 |
| Fraction 4 | 104 | 35 |

*Equivalent protein quantities were assayed to control for dilutional effects.

As shown in Table 1, immune complex leves of the serum were reduced by passage through the immunoadsorbent.

3. Therapeutic Use of Column to Treat Kaposi's Sarcoma

A patient with advanced disseminated Kaposi's sarcoma and acquired immune deficiency syndrome (AIDS) was treated with plasma perfusion over a protein A column prepared as described above. The immunologic and tumor changes observed during the treatment are reported below.

The patient was a 44 year old homosexual man with a history of extensive Kaposi's sarcoma and AIDS. Skin lesions were first noted on the feet and legs, with inguinal node involvement, 26 months prior to protein A therapy. At that time, weekly intravenous treatments with vinblastine were initiated; the dosage was adjusted according to the complete blood count. The Kaposi's sarcoma remained stable and regionalized to the lower extremities for 1 year, at which time a few scattered lesions slowly became apparent on the forearms and both calves. Six months later, because of enlargement of inguinal nodes and a new pubic lesion, chlorambucil, 2 mg b.i.d., was added. Within 2 months, the nodes decreased and skin lesions stabilized, and chlorambucil was discontinued. Disease activity again began to accelerate 4 months prior to protein A therapy, with new lesions forming on the trunk, face, legs, feet, arms, and hands, along with confluence of old lesions on the right tibia, despite continued vinblastine infusions. Dyspnea and dry cough became apparent 3 months later, with an X-ray film showing new bilateral basilar infiltrates. Open lung biopsy revealed extensive involvement of the lung with Kaposi's sarcoma. Additional skin lesions appeared almost daily, and the patient's condition continued to deteriorate.

At the time of admission of extracorporeal protein A perfusion treatment, the patient's white blood cell count was 7,500 cells/mm$^3$, with a differential of 70% polymorphonuclear leukocytes, 3% bands, 11% lymphocytes, 14% monocytes, and 2% eosinophils. The hemoglobin level was 8.3 g/dl, and the hematocrit 25.6%, with a platelet count of 87,000/mm$^3$. The total protein level was 5.3 g%, the albumin 2.8 g% and the IgG level was 1,170 mg%. Circulating immune complex (IgG-complex), measured using the solid-phase Clq-binding assay, were 4.7 μg equivalents of aggregated human gamma globulin (AHG). Complement levels were 55 mg% (C3) and 6 mg% (C4).

Immunofluorescent studies with monoclonal antibodies (Ortho-mune, Raritan, NJ) on circulating lymphocytes revealed 58% total T cells ($T_3$), 12% helper/inducer T cells ($T_4$), and 44% suppressor/cytotoxic T cells ($T_8$), with a $T_4/T_8$ ratio of 0.21.

Pulmonary function tests revealed a forced vital capacity of 2.46 L (51% of predicted) and forced expiratory volume, in 1 second, of 1.64 L (45% of predicted). Carbon monoxide diffusion capacity was 57% of normal. The arterial blood gases on room air were as follows: $Po_2$, 62 mm Hg; $Pco_2$, 41 mm Hg; $HCO_3$, 30.5 mEq/L; pH 7.48.

The extracorporeal immunoadsorption procedures were performed in the intensive care unit. A Swan-Ganz catheter was placed into the pulmonary artery to monitor hemodynamic changes. A continuous-flow plasm-cell separator (IBM 2997, Armonk, NY) was used to separate anticoagulated blood into cellular components and plasma. The cellular components were returned unprocessed. The plasma was perfused over a column containing 200 mg protein A covalently bound to silica prepared as described above, and returned to the patient. The protein A was isolated from pure cultures of Staphylococcus aureus Cowan I employing lysostaphin digestion. Protein A purity was determined by polyacrylamide gel electrophoresis, and IgG binding capacity was determined. The protein A was covalently coupled to silica, loaded into a biocompatible cartridge, and sterilized by exposure to ethylene oxide. Sterility was confirmed employing strips impregnated with spores of Bacillus subtilis (Raven Biological Laboratory, Omaha, NE). In addition, studies revealed that extensive washing of the column with 4 L of sterile, pryogen-free water, immediately prior to use, resulted in a lack of detectable pyrogens (Limulus amoebocyte lysate, Pyrogent ®; Mallinckrodt, Inc., St. Louis, MO). Each protein A treatment column had the capacity to bind approximately 1.5 g IgG from plasma. Plasma flow rates were between 10 and 20 ml/min. Three liters of plasma was perfused during each procedure. Three treatments were performed over 7 days on an every-other-day schedule. The patient was treated three times with extracorporeal perfusion of plasma over protein A. Three days after the last procedure the patient died of respitory distress and an autopsy was performed.

RESULTS

No major complications occurred during the treatment procedures. A mild drop (10-20 mm Hg) in systolic blood pressure was observed, along with sinus tachycardia up to 120 beats/min, but neither required therapy. Changes in body temperature were less than 1° C. The patient reported pain in tumor lesions on his right lower extremity during the last procedure; otherwise, no lesional discomfort was noted. The patient's pulmonary status remained stable throughout each procedure and, overall, the treatments were well tolerated.

No new lesions of the skin appeared after initiation of treatment. Grossly, about 20% of the skin lesions showed a slight decrease in size along with central necrosis. Erythematous halos appeared around those lesions and were apparent after the second treatment. Healing was initiated in a large, confluent ulcerated lesion of the right tibia. No measureable change in adenopathy was noted. Prior to treatments, intraoperative examination of the thorax during open lung biopsy revealed flat, indurated, hemorrhagic plaques involving the pleura, and widespread reddish nodular lesions of the lung parenchyma. At autopsy examination, 16 hours after the patient's death, those same pleural areas appeared to have definite central umbilication; the lung was more hemorrhagic, with a decrease in nodularity. Histologically, pretreatment tissue from the open lung biopsy revealed characteristic Kaposi's sarcoma, with nodular, hemorrhagic, densely cellular infiltrates of plump, spindled cells forming scant fascicles, and numerous abortive vascular spaces. Postmortem microscopic examination of the lung revealed a decrease in tumor cell density, reduction in nuclear size, and increasing collagen deposition between the tumor cells. Similar changes were observed in some of the responding skin lesions compared with pretreatment biopsy specimens.

Biopsies from skin tumor lesions taken prior to treatment showed no deposits of IgM, IgG, or IgA, nor of C3 or C4, as determined by direct immunofluorescence on frozen sections. Biopsies taken after the last procedure from the same lesions showed C3 deposits, but no deposition in immunoglobulins.

The changes in immunologic parameters are shown in Table 2. Of interest, the IgG-complex level increased from 2.6 μg equivalents of AHG prior to the third treatment to 6.5 μg equivalents of AHG 24 hours later.

TABLE 2

| Parameter | First procedure | Second procedure | Third procedure |
|---|---|---|---|
| IgG (mg %) | 1.170 | 820 | 808 |
| Immune complexes (IgG) (μg equivalents of AHG) | 4.7 | 2.3 | 6.5 |
| Complement (mg %) | 55(C3) 6(C4) | Not done | 74(C3) 5.5(C4) |
| Antilymphocyte antibody titer | 1:16 | None detectable | None detectable |
| $T_4/T_8$ ratio | 0.21 | 0.18 | 0.19 |
| Inhibitory factors | 1:16 | None detectable | None detectable |
| Circulating lymphocytes (per mm3) | 825 | 962 | 720 |

All values are pretreatment. AHG, aggregated human gamma globulin, measured as described by Hay et al. (1976) Clin. Exp. Immunol. 24:396-400.

There were no significant changes in hematologic values, except for a decrease of 46% in the platelet count over the treatment period.

Although the foregoing invention has been described in detail for purposes of clarity of understanding, it will be obvious that certain modifications may be practiced within the scope of the appended claims.

What is claimed is:

1. A method for treating a patient suffering from Kaposi's sarcoma, said method comprising extracorporeally contacting the patient's plasma with an immunoadsorbent material capable of binding immune complexes in order to effect removal of immune complexes from the patient's blood.

2. A method as in claim 1, wherein the immunoadsorbent is protein A covalently bound to an inert matrix.

3. A method as in claim 2, wherein the inert matrix is silica.

4. A method for treating a patient suffering from Kaposi's sarcoma, said method comprising the steps:
   (a) drawing blood from the patient;
   (b) contacting plasma from the patient's blood with an immunoadsorbent material capable of binding immune complexes in order to effect removal of said immune complexes; and
   (c) reinfusing the treated blood into the patient.

5. A method as in claim 4, wherein a continuous flow of blood is drawn from the patient and treated blood is returned while additional blood is drawn.

6. A method as in claim 5, wherein the flow of blood is continuously separated into cellular components and plasma, the plasma contacted with a protein A immunoadsorbent, and the cellular components and treated plasma reinfused into the patient.

7. A method as in claim 4, wherein the steps (a) through (c) are repeated periodically.

8. A method for treating a patient suffering from Kaposi's sarcoma, said method comprising:
   (a) recovering plasma from the patient;
   (b) contacting the plasma with an immunoadsorbent material comprising protein A covalently attached to an inert matrix; and
   (c) returning the plasma to the patient.

9. A method as in claim 8, wherein steps (a) through (c) are repeated periodically.

10. A method as in claim 9, wherein the plasma is recovered by drawing a continuous flow of blood from the patient, separating the blood into plasma and cellular components, and reinfusing the cellular components to the patient.

* * * * *